(12) United States Patent
Kim et al.

(10) Patent No.: US 8,303,943 B2
(45) Date of Patent: Nov. 6, 2012

(54) AMPHOLYTIC COPOLYMER BASED ON QUATERNIZED NITROGEN-CONTAINING MONOMERS

(75) Inventors: Son Nguyen Kim, Hemsbach (DE); Axel Jentzsch, Ludwigshafen (DE); Nathalie Bouillo, Baden-Baden (DE)

(73) Assignee: BASF SE, Ludwigsnafen (DE)

( * ) Notice: Subject to any disclaimer, the term of this patent is extended or adjusted under 35 U.S.C. 154(b) by 503 days.

(21) Appl. No.: 12/441,288

(22) PCT Filed: Sep. 14, 2007

(86) PCT No.: PCT/EP2007/059725
§ 371 (c)(1),
(2), (4) Date: Mar. 13, 2009

(87) PCT Pub. No.: WO2008/031892
PCT Pub. Date: Mar. 20, 2008

(65) Prior Publication Data
US 2010/0068156 A1    Mar. 18, 2010

(30) Foreign Application Priority Data

Sep. 15, 2006  (EP) .................................... 06120778
Jun. 29, 2007  (EP) .................................... 07111467

(51) Int. Cl.
*A61K 31/74* (2006.01)
(52) U.S. Cl. .................................................. 424/78.08
(58) Field of Classification Search ........................ None
See application file for complete search history.

(56) References Cited

U.S. PATENT DOCUMENTS

| | | | |
|---|---|---|---|
| 3,927,199 A | 12/1975 | Micchelli et al. | |
| 4,237,253 A | 12/1980 | Jacquet et al. | |
| 4,358,567 A | 11/1982 | Hayama et al. | |
| 6,277,386 B1 | 8/2001 | Kim et al. | |
| 6,361,768 B1 | 3/2002 | Galleguillos et al. | |
| 2003/0147929 A1 * | 8/2003 | Kim et al. | 424/401 |
| 2005/0053566 A1 | 3/2005 | Nguyen-Kim et al. | |
| 2005/0265950 A1 | 12/2005 | Chrisstoffels et al. | |
| 2006/0153793 A1 | 7/2006 | Chrisstoffels et al. | |
| 2006/0183822 A1 | 8/2006 | Nguyen-Kim et al. | |
| 2007/0116660 A1 | 5/2007 | Kim et al. | |
| 2007/0141013 A1 | 6/2007 | Nguyen-Kim et al. | |
| 2008/0199416 A1 | 8/2008 | Nguyen Kim et al. | |
| 2008/0227871 A1 | 9/2008 | Kim et al. | |
| 2009/0010865 A1 | 1/2009 | Kim et al. | |
| 2009/0257960 A1 | 10/2009 | Kim et al. | |
| 2010/0040573 A1 | 2/2010 | Garcia Castro et al. | |
| 2010/0174040 A1 | 7/2010 | Kim et al. | |

FOREIGN PATENT DOCUMENTS

| | | |
|---|---|---|
| CA | 2615804 | 1/2007 |
| EP | 0330174 | 8/1989 |
| GB | 2088209 | 6/1982 |
| JP | 2003-081739 A | 9/2001 |
| JP | 2005-516942 | 6/2005 |
| JP | 2007-514031 | 5/2007 |
| WO | WO-9535087 | 12/1995 |
| WO | WO 01/62809 | 8/2001 |
| WO | WO-0162809 | 8/2001 |
| WO | WO 0162809 A1 * | 8/2001 |
| WO | WO-2004022616 | 3/2004 |
| WO | WO-2004058837 | 7/2004 |
| WO | WO-2005005497 | 1/2005 |
| WO | WO-2005058988 | 6/2005 |
| WO | WO-2007010034 | 1/2007 |
| WO | WO-2007010035 | 1/2007 |
| WO | WO-2007012610 | 2/2007 |

OTHER PUBLICATIONS

U.S. Appl. No. 12/674,581, filed Feb. 22, 2010, Kim et al.
U.S. Appl. No. 12/865,755, filed Aug. 2, 2010, Kim et al.
U.S. Appl. No. 13/062,197, filed Mar. 3, 2011, Kim et al.

* cited by examiner

*Primary Examiner* — Paul Dickinson
(74) *Attorney, Agent, or Firm* — Connolly Bove Lodge & Hutz LLP

(57) ABSTRACT

The present invention relates to an ampholytic copolymer based on quaternized nitrogen-containing monomers which has a molar excess of cationogenic/cationic groups compared to anionogenic/anionic groups, to cosmetic or pharmaceutical compositions which comprise at least one such ampholytic copolymer, and to further uses of these copolymers.

21 Claims, No Drawings

AMPHOLYTIC COPOLYMER BASED ON QUATERNIZED NITROGEN-CONTAINING MONOMERS

CROSS REFERENCE TO RELATED APPLICATIONS

This application is a National Stage of PCT/EP2007/059725 filed Sep. 14, 2007 which in turn claims priority from European Application 06120778.3 filed Sep. 15, 2006 and European Application 07111467.2 filed Jun. 29, 2007, the entire contents of which are incorporated herein by reference.

The present invention relates to an ampholytic copolymer based on quaternized nitrogen-containing monomers which has a molar excess of cationogenic/cationic groups compared to anionogenic/anionic groups, to cosmetic or pharmaceutical compositions which comprise at least one such ampholytic copolymer, and to further uses of these copolymers.

Polymers with a relatively large number of ionically dissociable groups in the main chain and/or one side chain are referred to as polyelectrolytes. If these polymers have both anionogenic/anionic and cationogenic/cationic groups, then these are amphoteric polyelectrolytes or ampholytic polymers. Ampholytic polymers with an adequate number of dissociable groups are water-soluble or water-dispersible and have found diverse uses in the field of coatings, paper auxiliaries, hygiene products, during the manufacture of textiles, and specifically in pharmacy and cosmetics.

Cosmetically and pharmaceutically acceptable water-soluble polymers serve, for example in soaps, creams and lotions, as formulation agents, e.g. as thickeners, foam stabilizer or water absorbent or else to alleviate the irritative effect of other ingredients or to improve the dermal application of active ingredients. Their task in hair cosmetics consists in influencing the properties of the hair. In pharmacy, they serve, for example, as coatings or binders for solid drug forms. For hair cosmetics, film-forming polymers with ionic groups are used, for example, as conditioners in order to improve the dry and wet combability, the feel to the touch, the shine and the appearance of hair, and to impart antistatic properties to the hair. Depending on the intended use, water-soluble polymers with cationic or anionic functionalities are used here. Thus, polymers with cationic functional groups have, as a result of their structure, a high affinity to the negatively charged surface of the hair. Polymers with anionic functionalities, such as, for example, optionally crosslinked polyacrylic acid, serve, for example, as thickeners; in addition polymers containing carboxylate groups are used, for example, for setting hairstyles.

For hair cosmetics, film-forming polymers are also used as setting resins in order to impart hold to the hairstyle. Requirements for setting resins are, for example, strong hold at high atmospheric humidity, elasticity, ability to be washed out of the hair, compatibility in the formulation and a pleasant feel of the hair treated therewith. For setting hairstyles, use is made, for example, of vinyllactam homopolymers and copolymers and polymers containing carboxylate groups.

Difficulties often arise with the provision of products with a complex profile of properties. Thus, there is a need for polymers for hair cosmetic compositions which are capable for forming essentially smooth, nonsticky films which have to the hair a good setting effect (even at high atmospheric humidity) and, at the same time, impart good sensorily perceptible properties, such as elasticity and a pleasant feel, to the hair. If these polymers are to be used in hairspray formulations, then good propellent-gas compatibility, suitability for use in low-VOC formulations, good solubility in water or aqueous/alcoholic solvent mixtures and good ability to be washed out are also desired.

In many cases, the desired profile of properties can only be achieved by using a plurality of cosmetically active components, for example a plurality of polymers with ionic groups. However, there is often incompatibility between the various components, which can, for example, lead to it no longer being possible to produce clear formulations. The use of a plurality of polyelectrolytes which are inadequately compatible with one another can lead to undesired salting out. There is therefore a need for cosmetically and pharmaceutically compatible polyelectrolytes which are suitable when used as the sole polymer component for providing a certain profile of properties and/or which are compatible with a large number of different components.

U.S. Pat. No. 4,358,567 describes hair polymers with betaine structure which are obtainable by reacting a copolymer based on aminoalkyl(meth)acrylates with sodium or potassium monochloroacetate.

EP-A-0 330 174 describes a hair setting gel composition which comprises a partially or completely neutralized salt of a crosslinked carboxyl-group-containing polymer, an amphoteric resin and a solvent. The amphoteric resin may be copolymers with betaine structural units or copolymers which are obtainable by copolymerizing at least one monomer having acidic groups and at least one monomer having basic groups.

GB-A 2,088,209 describes a hair-treatment composition based on amphoteric polymers and anionic polymers. The amphoteric polymer here may comprise monomer units derived from dimethylaminoethyl methacrylate quaternized with dimethyl sulfate or diethyl sulfate.

WO 01/62809 describes a cosmetic composition which comprises at least one water-soluble or water-dispersible polymer which comprises, in incorporated form,
  a) 5 to 50% by weight of at least one $\alpha,\beta$-ethylenically unsaturated monomer with a tert-butyl group,
  b) 25 to 90% by weight of at least one N-vinylamide and/or N-vinyllactam,
  c) 0.5 to 30% by weight of at least one compound with a free-radically polymerizable, $\alpha,\beta$-ethylenically unsaturated double bond and at least one cationogenic and/or cationic group per molecule, and
  d) 0 to 30% by weight of at least one further $\alpha,\beta$-ethylenically unsaturated compound, which may be compounds with at least one anionogenic and/or anionic group per molecule.

U.S. Pat. No. 3,927,199 describes a hair-setting composition which comprises a film-forming binder resin based on a copolymer which comprises, in copolymerized form, 1) N-alkylacrylamides or -methacrylamides, 2) monomers containing acid groups and 3) at least one further comonomer.

U.S. Pat. No. 4,237,253 describes copolymers for hair-treatment compositions which comprise, in copolymerized form, 22 to 64 mol % of N,N-dimethylamino-2-ethyl methacrylate, 13 to 71 mol % of methyl methacrylate, 6 to 23 mol % of methacrylic acid and up to 22 mol % of further monomers.

WO 95/35087 describes an amphoteric hair setting polymer for use in hairsprays and gels which comprises, in copolymerized form, 40 to 90% by weight of a monomer containing hydroxyl groups, 1 to 20% by weight of a monomer containing acid groups and 1 to 20% by weight of a monomer containing amine groups.

WO 2004/058837 describes an ampholytic copolymer which is obtainable by free-radical copolymerization of a) at least one ethylenically unsaturated compound with at least one anionogenic and/or anionic group,
b) at least one ethylenically unsaturated compound with at least one cationogenic and/or cationic group,
c) at least one unsaturated amide-group-containing compound and, optionally, further comonomers. Also described are polyelectrolyte complexes which comprise one such ampholytic copolymer, and cosmetic or pharmaceutical compositions based on these ampholytic copolymers and polyelectrolyte complexes.

WO 2004/022616 describes the use of polymers which are obtainable by
(i) free-radically initiated copolymerization of monomer mixtures of
  (a) at least one cationic monomer or quaternizable monomer,
  (b) optionally, a water-soluble monomer,
  (c) optionally, a further free-radically copolymerizable monomer,
  (d) at least one monomer with at least two ethylenically unsaturated, nonconjugated double bonds acting as crosslinker, and
  (e) at least one regulator,
(ii) subsequent quaternization or protonation of the polymer if a nonquaternized or only partially quaternized monomer is used as monomer (a)
in hair cosmetic preparations.

WO 2005/005497 describes an aqueous polymer dispersion Pd) which is obtainable by free-radical polymerization of a monomer mixture M) comprising
a) at least one α,β-ethylenically unsaturated amide-group-containing compound of the general formula I

(I)

where
R² is a group of the formula CH₂=CR⁴— and R¹ and R³, independently of one another, are H, alkyl, cycloalkyl, heterocycloalkyl, aryl or hetaryl, or R¹ and R³, together with the amide group to which they are bonded, are a lactam with 5 to 8 ring atoms,
b) at least one free-radically polymerizable crosslinking compound with at least two α,β-ethylenically unsaturated double bonds per molecule,
c) at least one compound with a free-radically polymerizable α,β-ethylenically unsaturated double bond and at least one cationogenic and/or cationic group per molecule,
in an aqueous medium in the presence of at least one polymeric anionic dispersant D). They are suitable as conditioners for cosmetic preparations, in particular shampoos.

WO 2005/058988 describes ampholytic copolymers which comprise a molar excess of anionogenic and/or anionic groups and which are obtainable by free-radical polymerization of
a) at least one branched $C_3$-$C_5$-alkyl acrylate,
b) acrylic acid and/or methacrylic acid
c) a monomer composition comprising
  c1) at least one compound with a free-radically polymerizable, α,β-ethylenically unsaturated double bond and at least one anionogenic and/or anionic group per molecule and
  c2) at least one compound with a free-radically polymerizable, α,β-ethylenically unsaturated double bond and at least one cationogenic and/or cationic group per molecule, where the molar ratio of anionogenic and anionic groups in component c1) to cationogenic and cationic groups in component c2) is about 1:1.

The international applications WO 2007/010034 (PCT/EP2006/064504), WO 2007/010035 (PCT/EP2006/064506) and WO 2007/012610 (PCT/EP2006/064507) which were unpublished at the priority date of the invention, describe anionically ampholytic copolymers, cationically ampholytic copolymers and their use as rheology modifiers for hair cosmetic compositions.

Despite extensive efforts, there continues to be a need to improve the polymers known from the prior art for producing elastic hairstyles coupled with strong hold (even at high atmospheric humidity). For promising use in hairspray formulations, good propellent-gas compatibility, good solubility in water or aqueous/alcoholic solvent mixtures, suitability for use in low-VOC formulations and good ability to be washed out are also desired. Good properties are likewise desired with regard to conditioning of the hair in its sensorily perceptible properties such as feel, volume, handleability etc. In addition, the polymers should be characterized by good compatibility with other formulation constituents.

Surprisingly, it has been found that of suitability for the abovementioned requirements are, in particular, ampholytic copolymers which have a molar excess of cationogenic/cationic groups compared to anionogenic/anionic groups and which are obtainable by free-radical polymerization of
a) at least one α,β-ethylenically unsaturated monomer of the general formula I

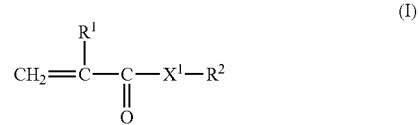

(I)

in which
R¹ is hydrogen or $C_1$-$C_8$-alkyl,
X¹ is O or NR³, where R³ is hydrogen, alkyl, cycloalkyl, aryl or hetaryl,
R² is branched $C_3$-$C_5$-alkyl,
b) at least one compound with a free-radically polymerizable, α,β-ethylenically unsaturated double bond and at least one cationogenic and/or cationic group per molecule, with the proviso that at least some of the compounds b) have at least one quaternary nitrogen atom,
c) at least one compound with a free-radically polymerizable, α,β-ethylenically unsaturated double bond and at least one anionogenic and/or anionic group per molecule and
d) optionally at least one amide-group-containing monomer which is chosen from α,β-ethylenically unsaturated amide-group-containing compounds of the general formula II

(II)

where one of the radicals $R^4$ to $R^6$ is a group of the formula $CH_2$=$CR^7$— where $R^7$=H or $C_1$-$C_4$-alkyl and the other radicals $R^4$ to $R^6$, independently of one another, are H, alkyl, cycloalkyl, heterocycloalkyl, aryl or hetaryl, where $R^4$ and $R^5$, together with the amide group to which they are bonded, may also be a lactam with 5 to 8 ring atoms, where $R^5$ and $R^6$, together with the nitrogen atom to which they are bonded, may also be a five- to seven-membered heterocycle.

In one preferred embodiment of the present invention, the ampholytic copolymer comprises at least one monomer of component d) in copolymerized form.

Within the scope of the present invention, the expression alkyl comprises straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include, in particular, methyl, ethyl, propyl, isopropyl, n-butyl, isobutyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 2-ethylpentyl, 1-propylbutyl, etc.

Branched $C_3$-$C_5$-alkyl is preferably isopropyl, isobutyl, sec-butyl, tert-butyl, 1-methylbutyl, 2-methylbutyl, 3-methylbutyl, 1,2-dimethylpropyl, 1,1-dimethylpropyl, 2,2-dimethylpropyl, 1-ethylpropyl. Preference is given to tert-butyl.

Suitable longer-chain $C_8$-$C_{30}$-alkyl groups are straight-chain and branched alkyl groups. These are preferably predominantly linear alkyl radicals, as also occur in natural or synthetic fatty acids and fatty alcohols, and oxo alcohols. These include, for example, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignoceryl, cerotinyl, melissyl(ene), etc.

Suitable longer-chain $C_8$-$C_{30}$-alkenyl groups are straight-chain and branched alkenyl groups which may be mono-, di- or polyunsaturated. These are preferably predominantly linear alkenyl radicals, as also occur in natural or synthetic fatty acids and fatty alcohols, and oxo alcohols. These include, in particularly octenyl, nonenyl, decenyl, undecenyl, dodecenyl, tridecenyl, tetradecenyl, pentadecenyl, hexadecenyl, heptadecenyl, octadecenyl, nonadecenyl, n-eicosenyl, n-docosenyl, n-tetracosenyl, hexacosenyl, triacontenyl, etc.

Cycloalkyl is preferably $C_5$-$C_8$-cycloalkyl, such as cyclopentyl, cyclohexyl, cycloheptyl or cyclooctyl.

Aryl comprises unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

The term "N,N-dialkylamides" also comprises compounds in which the amide nitrogen is part of a five- to seven-membered heterocycle which can additionally comprise a heteroatom selected from oxygen, sulfur and $NR^a$, in which $R^a$ is hydrogen, alkyl or cycloalkyl.

In the text below, compounds which can be derived from acrylic acid and methacrylic acid are sometimes referred to in abbreviated form by adding the syllable "(meth)" to the compound derived from acrylic acid.

Within the scope of the present invention, water-soluble monomers and polymers are understood as meaning monomers and polymers which dissolve in water to at least 1 g/l at 20° C. Water-dispersible monomers and polymers are understood as meaning monomers and polymers which disintegrate into dispersible particles under the application of shear forces, for example by stirring. Hydrophilic monomers are preferably water-soluble or at least water-dispersible. The copolymers A) according to the invention are generally water-soluble.

In one specific embodiment, the copolymers according to the invention have no silicon-atom-containing groups.

The monomer mixture used for producing the copolymers according to the invention has monomers with cationogenic and/or cationic groups and monomers with anionogenic and/or anionic groups. The amount of monomers with ionogenic and/or ionic groups used for the polymerization is such that, based on the monomers used overall for the polymerization, the molar fraction of cationogenic and cationic groups is greater than the molar fraction of anionogenic and anionic groups. The copolymers according to the invention therefore have, on average, a molar excess of cationogenic/cationic groups compared to anionogenic/anionic groups. Preferably, the molar ratio of cationogenic/cationic groups to anionogenic/anionic groups is at least 1.01:1, particularly preferably at least 1.2:1, in particular at least 1.4:1, specifically at least 1.5:1, more specifically at least 2:1.

Surprisingly, it has been found that copolymers with particularly advantageous properties are obtained if, for the polymerization, use is made of monomers with cationic groups which have at least one quaternary nitrogen atom. Preferably, the cationogenic and/or cationic groups of component b) are nitrogen-containing groups, such as primary, secondary and tertiary amino groups, and quaternary ammonium groups. According to the invention, at least some of the monomers b) have quaternary ammonium groups. Quaternary ammonium groups, i.e. charged cationic groups, can be produced from the amine nitrogens by quaternization with alkylating agents. These include $C_1$-$C_4$-alkyl halides or sulfates, such as ethyl chloride, ethyl bromide, methyl chloride, methyl bromide, dimethyl sulfate and diethyl sulfate. A preferred quaternizing agent is diethyl sulfate. Charged cationic groups (but no quaternary ammonium groups within the meaning of the invention) can be produced from the amine nitrogens also by protonation with acids. Suitable acids are, for example, carboxylic acids, such as lactic acid, or mineral acids, such as phosphoric acid, sulfuric acid and hydrochloric acid.

Monomer a)

The copolymers according to the invention comprise, in copolymerized form, at least one compound which is preferably chosen from isopropyl acrylate, isopropyl methacrylate, isopropylacrylamide, isopropylmethacrylamide, isobutyl acrylate, isobutyl methacrylate, isobutylacrylamide, isobutylmethacrylamide, sec-butyl acrylate, sec-butyl methacrylate, sec-butylacrylamide, sec-butylmethacrylamide, tert-butyl acrylate, tert-butyl methacrylate, tert-butylacrylamide, tert-butylmethacrylamide, 1-methylbutyl acrylate, 1-methylbutyl methacrylate, 1-methylbutylacrylamide, 1-methylbutylmethacrylamide, 2-methylbutyl acrylate, 2-methylbutyl methacrylate, 2-methylbutylacrylamide, 2-methylbutylmethacrylamide, 3-methylbutyl acrylate, 3-methylbutyl methacrylate, 3-methylbutylacrylamide, 3-methylbutylmethacrylamide, 1,1-dimethylpropyl acrylate, 1,1-dimethylpropyl methacrylate, 1,1-dimethylpropylacrylamide, 1,1-dimethylpropylmethacrylamide, 2,2-dimethylpropyl acrylate, 2,2-dimethylpropyl methacrylate, 2,2-dimethylpropylacrylamide, 2,2-dimethylpropylmethacrylamide, and mixtures thereof. Particular preference is given to tert-butyl acrylate and mixtures which comprise tert-butyl acrylate.

The copolymers according to the invention comprise preferably 15 to 90% by weight, particularly preferably 20 to 85% by weight, in particular 25 to 75% by weight, based on the total weight of the monomers used for the polymerization, of at least one monomer a) in copolymerized form.

Monomer b)

The copolymers according to the invention comprise, as compound b), at least one compound with a free-radically polymerizable, α,β-ethylenically unsaturated double bond and at least one cationogenic and/or cationic group per molecule in copolymerized form. According to the invention, at least some of compounds b) have a quaternary nitrogen atom.

The copolymers according to the invention comprise preferably 3 to 98% by weight, particularly preferably 5 to 90% by weight, in particular 7 to 80% by weight, based on the total weight of the monomers used for the polymerization, of at least one monomer b) in copolymerized form.

Preferably, 0 to 100% by weight, particularly preferably 5 to 100% by weight, for example 10 to 99% by weight of monomers b), based on the total weight of monomers b), are present in quaternized form.

Preferably, component b) is chosen from esters of α,β-ethylenically unsaturated mono- and dicarboxylic acids with amino alcohols which may be mono- or dialkylated on the amine nitrogen, amides of α,β-ethylenically unsaturated mono- and dicarboxylic acids with diamines which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds, the quaternization products of these monomers and mixtures thereof.

In a preferred embodiment, component b) comprises at least one N-vinylimidazole compound as vinyl-substituted heteroaromatic compound. In a specific embodiment, component b) is chosen from N-vinylimidazole compounds and mixtures which comprise at least one N-vinylimidazole compound.

Suitable N-vinylimidazole compounds are compounds of the formula

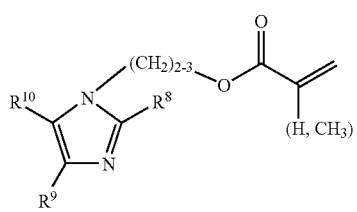

in which $R^8$ to $R^{10}$, independently of one another, are hydrogen, $C_1$-$C_4$-alkyl or phenyl. Preferably, $R^8$ to $R^{10}$ are hydrogen.

Furthermore, the copolymer preferably comprises, in copolymerized form, as monomer b) at least one N-vinylimidazole compound of the general formula (III)

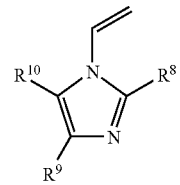

(III)

in which $R^8$ to $R^{10}$, independently of one another, are hydrogen, $C_1$-$C_4$-alkyl or phenyl.

Examples of compounds of the general formula (III) are given in table 1 below:

TABLE 1

| $R^8$ | $R^9$ | $R^{10}$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

1-Vinylimidazole (N-vinylimidazole) and mixtures which comprise N-vinylimidazole are preferred as monomer b).

Suitable monomers b) are also the compounds obtainable by protonation or quaternization of the abovementioned N-vinylimidazole compounds. Examples of such charged monomers b) are quaternized vinylimidazoles, in particular 3-methyl-1-vinylimidazolium chloride, methosulfate and ethosulfate. Suitable acids and alkylating agents are those listed above.

Suitable compounds b) are also the esters of α,β-ethylenically unsaturated mono- and dicarboxylic acids with amino alcohols. Preferred amino alcohols are $C_2$-$C_{12}$-amino alcohols which are $C_1$-$C_8$-mono- or -dialkylated on the amine nitrogen. Suitable as acid component of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof as acid component.

Preferred monomers b) are N-tert-butylaminoethyl(meth)acrylate, N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate. Particular preference is given to N-tert-butylaminoethyl(meth)acrylate and N,N-dimethylaminoethyl(meth)acrylate. Preferred monomers b) are, in particular, also the quaternization products of the abovementioned compounds.

Suitable monomers b) are also the amides of the abovementioned α,β-ethylenically unsaturated mono- and dicarboxylic acids with diamines which have at least one primary or secondary amino group. Preference is given to diamines which have one tertiary and one primary or secondary amino group.

Preferred monomers b) are, for example, N-[tert-butylaminoethyl](meth)acrylamide, N-[2-dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide. Particular preference is given to N-[3-(dimethylamino)propyl]acrylamide and N-[3-(dimethylamino)propyl]methacrylamide (DMAPMAM).

A specific embodiment relates to copolymers A) which comprise, in copolymerized form, N-[3-(dimethylamino)propyl]acrylamide and N-[3-(dimethylamino)propyl]methacrylamide. In a very specific embodiment, component b) consists only of N-[3-(dimethylamino)propyl]acrylamide and/or N-[3-(dimethylamino)propyl]methacrylamide.

Suitable monomers b) are also N,N-diallylamines and N,N-diallyl-N-alkylamines and their acid addition salts and quaternization products. Alkyl here is preferably $C_1$-$C_{24}$-alkyl. Preference is given to N,N-diallyl-N-methylamine and N,N-diallyl-N,N-dimethylammonium compounds, such as, for example, the chlorides and bromides. Particular preference is given to N,N-diallyl-N-methylamine.

Suitable monomers b) are also vinyl- and allyl-substituted nitrogen heterocycles different from vinylimidazoles, such as 2- and 4-vinylpyridine, 2- and 4-allylpyridine, and the salts thereof.

Preferably, component b) comprises at least one monomer which is chosen from N,N-dimethylaminoethyl(meth)acrylate, N-[3-(dimethylamino)propyl](meth)acrylamide, quaternized N,N-dimethylaminoethyl(meth)acrylate, quaternized N-[3-(dimethylamino)propyl](meth)acrylamide and mixtures thereof.

Furthermore, component b) preferably comprises N,N-dimethylaminoethyl(meth)acrylate quaternized with methyl chloride, dimethyl sulfate or diethyl sulfate. Here and in the text below, the terms "quat DMAEMA" and "Quat 311" are used synonymously with regard to the term "dimethylaminoethyl methacrylate quaternized with diethyl sulfate". Specifically, component b) comprises N,N-dimethylaminoethyl (meth)acrylate quaternized with diethyl sulfate.

The copolymers according to the invention comprise preferably 2 to 97% by weight, particularly preferably 3 to 96% by weight, in particular 4 to 60% by weight, based on the total weight of the monomers used for the polymerization, of at least one monomer b) in copolymerized form.

Monomer c)

The copolymers according to the invention comprise, as compound c), at least one compound with a free-radically polymerizable, α,β-ethylenically unsaturated double bond and at least one anionogenic and/or anionic group per molecule. Component c) is preferably used in an amount of 0.1 to 30% by weight, particularly preferably 1 to 25% by weight, in particular 1.5 to 20% by weight.

Preferably, component c) comprises at least one compound which is chosen from monoethylenically unsaturated carboxylic acids, sulfonic acids, phosphonic acids and mixtures thereof.

Monomers c) include monoethylenically unsaturated mono- and dicarboxylic acids having 3 to 25, preferably 3 to 6, carbon atoms, which may also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. Monomers c) also include the half-esters of monoethylenically unsaturated dicarboxylic acids having 4 to 10, preferably 4 to 6, carbon atoms, e.g. of maleic acid, such as monomethyl maleate. Monomers c) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosphonic acid. Monomers c) also include the salts of the abovementioned acids, in particular the sodium, potassium and ammonium salts, and the salts with amines. The monomers c) can be used as such or as mixtures with one another. The stated weight fractions all refer to the acid form.

Preferably, component c) comprises at least one compound which is chosen from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid, 2-acrylamido-2-methylpropanesulfonic acid, vinylphosphonic acid and mixtures thereof.

Component c) particularly comprises at least one compound c) which is chosen from acrylic acid, methacrylic acid and mixtures thereof. In a specific embodiment, component c) comprises methacrylic acid or consists of methacrylic acid.

Monomer d)

The copolymers according to the invention comprise preferably 5 to 95% by weight, particularly preferably 10 to 90% by weight, based on the total weight of the compounds used for the polymerization, of at least one monomer d) in copolymerized form.

Preferably, the compounds of component d) are chosen from primary amides of α,β-ethylenically unsaturated monocarboxylic acids, N-vinylamides of saturated monocarboxylic acids, N-vinyllactams, N-alkyl- and N,N-dialkylamides of α,β-ethylenically unsaturated monocarboxylic acids and mixtures thereof.

Preferred monomers d) are N-vinyllactams and derivatives thereof which may, for example, have one or more alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

Particular preference is given to using N-vinylpyrrolidone and/or N-vinylcaprolactam.

Suitable monomers d) are also acrylamide and methacrylamide.

Suitable N-alkyl- and N,N-dialkylamides of α,β-ethylenically unsaturated monocarboxylic acids which, in addition to the carbonyl carbon atom of the amide group, have at most 7 further carbon atoms are, for example, N-methyl(meth)acrylamide, N-ethyl(meth)acrylamide, N-propyl(meth)acrylamide, N-(n-butyl)(meth)acrylamide, N-tert-butyl(meth)acrylamide, n-pentyl(meth)acrylamide, n-hexyl(meth)acrylamide, n-heptyl(meth)acrylamide, N,N-dimethyl(meth)acrylamide, N,N-diethyl(meth)acrylamide, piperidinyl(meth)acrylamide, morpholinyl(meth)acrylamide and mixtures thereof.

Suitable N—$C_8C_{30}$-alkyl- and N—$(C_1$-$C_{30})$alkyl-N—$(C_8$-$C_{30})$alkyl 2-amides c) are, for example, n-octyl(meth)

acrylamide, 1,1,3,3-tetramethylbutyl(meth)acrylamide, 2-ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arachinyl(meth)acrylamide, behenyl(meth)acrylamide, lignocerenyl(meth)acrylamide, cerotinyl(meth)acrylamide, melissyl(meth)acrylamide, palmitoleinyl(meth)acrylamide, oleyl(meth)acrylamide, linolyl(meth)acrylamide, linolenyl (meth)acrylamide, stearyl(meth)acrylamide, lauryl(meth) acrylamide, N-methyl-N-(n-octyl)(meth)acrylamide, N,N-di-(n-octyl)(meth)acrylamide and mixtures thereof.

Open-chain N-vinylamide compounds suitable as monomers d) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof. Preference is given to using N-vinylformamide.

Also suitable as monomers d) are compounds of the formula

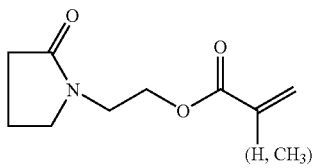

Particular preference is given to using N-vinylpyrrolidone, N-vinylcaprolactam, N-vinylformamide and the compounds of the above formula.

Monomer e)

The copolymers according to the invention can additionally comprise, in copolymerized form, at least one monomer e) that is different from components a) to d) and copolymerizable therewith.

Preferably, component e) is chosen from esters of α,β-ethylenically unsaturated mono- and dicarboxylic acids with $C_1$-$C_{30}$-alkanols, unsaturated $C_8$-$C_{30}$-fatty alcohols and $C_2$-$C_{30}$-alkanediols different from component a), amides of α,β-ethylenically unsaturated mono- and dicarboxylic acids with $C_2$-$C_{30}$-amino alcohols which have a primary or secondary amino group, esters of vinyl alcohol and allyl alcohol with $C_1$-$C_{30}$-monocarboxylic acids, vinyl ethers, vinylaromatics, vinyl halides, vinylidene halides, $C_2$-$C_8$-monoolefins, non-aromatic hydrocarbons with at least two conjugated double bonds and mixtures thereof.

Suitable additional monomers e) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers e) are also 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethyl hexylmethacrylamide.

Suitable monomers e) are also polyether acrylates, which, within the scope of this invention, are generally understood as meaning esters of α,β-ethylenically unsaturated mono- and dicarboxylic acids with polyetherols. Suitable polyetherols are linear or branched substances having terminal hydroxyl groups which comprise ether bonds. Generally, they have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for producing alkylene oxide copolymers are, for example, ethylene oxide, propylene oxide, epichlorohydrin, 1,2- and 2,3-butylene oxide. The alkylene oxide copolymers can comprise the copolymerized alkylene oxide units in random distribution or in the form of blocks. Preference is given to ethylene oxide/propylene oxide copolymers.

As component e), preference is given to polyether acrylates of the general formula IV

in which the order of the alkylene oxide units is arbitrary, k and l, independently of one another, are an integer from 0 to 1000, where the sum of k and l is at least 5, $R^{11}$ is hydrogen, $C_1$-$C_{30}$-alkyl or $C_5$-$C_8$-cycloalkyl, $R^{12}$ is hydrogen or $C_1$-$C_8$-alkyl, $Y^2$ is O or $NR^{13}$, where $R^{13}$ is hydrogen, $C_1$-$C_{30}$-alkyl or $C_5$-$C_8$-cycloalkyl.

Preferably, k is an integer from 1 to 500, in particular 3 to 250. Preferably, l is an integer from 0 to 100.

Preferably, $R^{12}$ is hydrogen, methyl, ethyl, n-propyl, isopropyl, n-butyl, sec-butyl, tert-butyl, n-pentyl or n-hexyl, in particular hydrogen, methyl or ethyl.

Preferably, $R^{11}$ in formula IV is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably, $Y^2$ in formula IV is O or NH.

Suitable polyether acrylates e) are, for example, the polycondensation products of the abovementioned α,β-ethylenically unsaturated mono- and/or dicarboxylic acids and their acid chlorides, amides and anhydrides with polyetherols. Suitable polyetherols can be prepared easily by reacting ethylene oxide, 1,2-propylene oxide and/or epichlorohydrin with a starter molecule such as water or a short-chain alcohol $R^{11}$—OH. The alkylene oxides can be used individually, alternately after one another or as a mixture. The polyether acrylates e) can be used alone or in mixtures for producing the polymers used according to the invention.

Suitable additional monomers e) are methyl(meth)acrylate, methyl ethacrylate, ethyl(meth)acrylate, ethyl ethacrylate, n-butyl(meth)acrylate, tert-butyl methacrylate, tert-butyl ethacrylate, n-octyl(meth)acrylate, 1,1,3,3-tetramethylbutyl(meth)acrylate, 2-ethylhexyl(meth)acrylate, n-nonyl(meth)acrylate, n-decyl(meth)acrylate, n-undecyl (meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arachinyl (meth)acrylate, behenyl(meth)acrylate, lignocerenyl(meth) acrylate, cerotinyl(meth)acrylate, melissyl(meth)acrylate, palmitoleinyl(meth)acrylate, oleyl(meth)acrylate, linolyl (meth)acrylate, linolenyl(meth)acrylate, stearyl(meth)acrylate, lauryl(meth)acrylate and mixtures thereof. Preferred monomers e) are the esters of α,β-ethylenically unsaturated mono- and dicarboxylic acids with $C_1$-$C_4$-alkanols.

Suitable additional monomers e) are also vinyl acetate, vinyl propionate, vinyl butyrate and mixtures thereof.

Suitable additional monomers e) are also ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The abovementioned additional monomers e) can be used individually or in the form of any mixtures.

Preferably, the copolymers according to the invention comprise, in copolymerized form, at least one compound e) which is chosen from $C_1$-$C_3$-alkyl methacrylates, hydroxy-$C_1$-$C_3$-alkyl methacrylates and mixtures thereof. Particular preference is given to ethyl methacrylate, hydroxyethyl methacrylate and mixtures thereof. In particular, ethyl methacrylate is used. The copolymers according to the invention comprise these copolymerized monomers preferably in an amount of from 0 to 50% by weight, particularly preferably 0 to 45% by weight, based on the total weight of the compounds used for the polymerization.

The copolymers according to the invention comprise preferably from 0 to 25% by weight, particularly preferably from 0 to 20% by weight, in particular from 0 to 15% by weight, based on the total weight of the monomers used for the polymerization, of at least one monomer e) in copolymerized form. If a monomer e) is used, then it is preferably in an amount of at least 0.1% by weight, particularly preferably at least 1% by weight and in particular at least 5% by weight.
Crosslinker f)

The copolymers according to the invention can, if desired, comprise at least one crosslinker, i.e. a compound with two or more than two ethylenically unsaturated, nonconjugated double bonds, in copolymerized form.

Preferably, crosslinkers are used in an amount of from 0.01 to 3% by weight, particularly preferably from 0.01 to 2% by weight, especially from 0.1 to 2% by weight and specifically from 0.1 to 1% by weight, based on the total weight of the monomers used for the polymerization.

Suitable crosslinkers f) are, for example, acrylic esters, methacrylic esters, allyl ethers or vinyl ethers of at least dihydric alcohols. The OH groups of the parent alcohols here may be completely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiapentane-1,5-diol, and polyethylene glycols, polypropylene glycols and polytetrahydrofurans with molecular weights of in each case from 200 to 10 000. Apart from the homopolymers of ethylene oxide and propylene oxide, it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. The polyhydric alcohols can of course also be used following reaction with ethylene oxide or propylene oxide as the corresponding ethoxylates or propoxylates, respectively. The polyhydric alcohols can also firstly be converted to the corresponding glycidyl ethers by reaction with epichlorohydrin.

Further suitable crosslinkers f) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric unsaturated alcohols with polybasic carboxylic acids, for example malonic acid, tartaric acid, trimellitic acid, phthalic acid, terephthalic acid, citric acid or succinic acid.

Further suitable crosslinkers f) are esters of unsaturated carboxylic acids with the above-described polyhydric alcohols, for example oleic acid, crotonic acid, cinnamic acid or 10-undecenoic acid.

Further suitable crosslinkers f) are urethane diacrylates and urethane polyacrylates, as are commercially available, for example, under the name Laromer®.

Suitable crosslinkers f) are, furthermore, straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable as crosslinkers f) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable as crosslinker f) are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Further suitable crosslinkers f) are divinyldioxane, tetraallylsilane or tetravinylsilane.

Mixtures of the abovementioned compounds f) can of course also be used. Preference is given to using water-soluble crosslinkers f).

Particularly preferably used crosslinkers f) are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Very particularly preferred crosslinkers f) are pentaerythritol triallyl ether, methylenebisacrylamide, N,N'-divinylethyleneurea, triallylamine and triallylmonoalkylammonium salts and acrylic esters of glycol, butanediol, trimethylolpropane or glycerol or acrylic esters of glycol, butanediol, trimethylolpropane or glycerol reacted with ethylene oxide and/or epichlorohydrin.

Preference is given to copolymers which comprise, in copolymerized form, 20 to 94.5% by weight, particularly preferably 25 to 85% by weight, of at least one compound a), 5 to 79.5% by weight, particularly preferably 10 to 35% by weight, in particular 13 to 30% by weight, of at least one compound b), 0.5 to 25% by weight, particularly preferably 1 to 20% by weight, in particular 2 to 15% by weight, of at least one compound c), 0 to 74.5% by weight, particularly preferably 1 to 60% by weight, in particular 5 to 50% by weight, of at least one compound d), 0 to 25% by weight, particularly preferably 0.1 to 20% by weight, in particular 1 to 15% by weight, of at least one compound e), 0 to 5% by weight, particularly preferably 0.01 to 3% by weight, in particular 0.1 to 2% by weight, of at least one crosslinker f).

A preferred embodiment covers copolymers which consist of repeat units of tert-butyl(meth)acrylate, at least one compound b) which is chosen from N,N-dimethylaminoethyl(meth)acrylate, N-[3-(dimethylamino)propyl](meth)acrylamide, N-(tert-butyl)aminoethyl(meth)acrylate, N-vinylimidazole and mixtures thereof, where at least some of the compounds b) are quaternized, acrylic acid and/or methacrylic acid, vinylpyrrolidone and/or vinylcaprolactam.

A further preferred embodiment covers copolymers which consist of repeat units of tert-butyl acrylate, N,N-dimethylaminoethyl methacrylate or N-[3-(dimethylamino)propyl]methacrylamide, quaternized N,N-dimethylaminoethyl methacrylate or quaternized N-[3-(dimethylamino)propyl]methacrylamide, methacrylic acid, vinylpyrrolidone.

In a specific embodiment, for the preparation of the abovementioned copolymers, use is made of partially or completely quaternized monomers b), where the quaternizing agent used was dimethyl sulfate or diethyl sulfate, in particular diethyl sulfate.

The copolymers according to the invention are prepared by customary methods known to the person skilled in the art, e.g. by solution polymerization, precipitation polymerization, suspension polymerization or emulsion polymerization. Also suitable is the W/W polymerization in water with a suitable displacement agent, e.g. a salt, such as NaCl.

Preferred solvents for the solution polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of the dihydric alcohols, diethylene glycol, triethylene glycol, polyethylene glycols with number-average molecular weights up to about 3000, glycerol and dioxane. Particular preference is given to the polymerization in water or in an alcohol or a water/alcohol mixture, for example in a water/ethanol mixture. The polymerization temperatures in the case of the solution polymerization are preferably in a range from about 30 to 120° C., particularly preferably 40 to 100° C.

The precipitation polymerization takes place preferably in a largely anhydrous, aprotic solvent or solvent mixture, preferably in ethyl acetate and/or n-butyl acetate. A largely anhydrous, aprotic solvent or solvent mixture is understood as meaning a solvent or solvent mixture with a water content of at most 5% by weight.

Preferably, the precipitation polymerization takes place at a temperature in the range from 70 to 140° C., preferably 75 to 100° C., in particular from 80 to 95° C. The resulting polymer particles precipitate out of the reaction solution and can be isolated by customary methods, such as filtration by means of subatmospheric pressure. For the precipitation polymerization, surface-active polymeric compounds, preferably based on polysiloxane, can be used. In the case of the precipitation polymerization, the polymers obtained usually have higher molecular weights than in the case of the solution polymerization.

The polymerization usually takes place under atmospheric pressure, although it can also proceed under reduced pressure or elevated pressure. A suitable pressure range is between 1 and 5 bar.

To produce the polymers, the monomers can be polymerized with the help of initiators which form free radicals.

Initiators which may be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane)dihydrochloride or 2,2'-azobis(2-methylbutyronitrile). Also suitable are initiator mixtures or redox initiator systems, such as, for example, ascorbic acid/iron(II)-sulfate/sodium peroxodisulfate, tert-butyl hydroperoxide/sodium disulfite, tert-butyl hydroperoxide/sodium hydroxymethanesulfinate, $H_2O_2/Cu^I$.

The polymerization can in principle take place at the pH which arises as a result of the monomers used. If, for the polymerization, at least one N-vinyllactam is used (=component d)), then the pH of the polymerization medium is preferably adjusted to a value of from 5 to 8, preferably 6 to 7. It is advantageous to then keep the pH in this range during the polymerization. Of suitability for adjusting the pH before, during or after the polymerization are, in principle, all inorganic or organic bases (and, optionally, acids), in particular those which, apart from possible salt formation, do not enter into a reaction with the monomers. Suitable bases are, for example, alkali metal and alkaline earth metal hydroxides, tertiary amines, such as triethylamine, and amino alcohols, such as triethanolamine, methyldiethanolamine or dimethylethanolamine. To adjust the pH, preference is given to using at least one tertiary amine, which is chosen in particular from N,N-dimethylethanolamine, N-methyldiethanolamine, triethanolamine and mixtures thereof.

To adjust the molecular weight, the polymerization can take place in the presence of at least one regulator. Regulators which can be used are the customary compounds known to the person skilled in the art, such as, for example, sulfur compounds, e.g. mercaptoethanol, 2-ethylhexyl thioglycolate, thioglycolic acid or dodecyl mercaptan, and tribromochloromethane or other compounds which have a regulating effect on the molecular weight of the resulting polymers. A preferred regulator is cysteine.

The K value of the copolymers according to the invention is 18 or higher, preferably 25 or higher, particularly preferably 42 or higher. The K value of the copolymers according to the invention is 120 or lower, preferably 80 or lower, particularly preferably 70 or lower. K values in the range from 42 to 70 are most preferred (determination in accordance with Fikentscher, Cellulosechemie, Vol. 13, pp. 58 to 64 (1932)). The K value determination takes place here as 1% strength solution of the copolymer in N-methylpyrrolidone.

For hydrous compositions, K values in the range from 28 to 42 are also preferred.

To achieve the purest possible polymers with a low residual monomer content, the polymerization (main polymerization) can be followed by an afterpolymerization step. The afterpolymerization can take place in the presence of the same initiator system as the main polymerization, or a different one. Preferably, the afterpolymerization takes place at least at the same temperature as, preferably at a higher temperature than, the main polymerization. If desired, after the polymerization or between the first and the second polymerization step, the reaction mixture can be subjected to stripping with steam or to steam distillation.

If, during the production of the polymers, an organic solvent is used, this can be removed by customary methods known to the person skilled in the art, e.g. by distillation at reduced pressure.

The resulting liquid polymer compositions can be converted to powder form by various drying methods, such as, for example, spray-drying, fluidized spray drying, roller drying or freeze drying. Preference is given to using spray-drying. The polymer dry powders obtained in this way can advantageously be converted again to an aqueous solution or dispersion by dissolution or redispersion, respectively, in water. Pulverulent copolymers have the advantage of better storability, easier transportability and generally exhibit a lower propensity for microbial attack.

The invention further provides a cosmetic or pharmaceutical composition comprising
A) at least one ampholytic copolymer, as defined above, and
B) at least one cosmetically acceptable carrier.

The compositions according to the invention preferably have a cosmetically or pharmaceutically acceptable carrier B) which is chosen from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols different from iii),
v) saturated acyclic and cyclic hydrocarbons,
vi) fatty acids,
vii) fatty alcohols,
viii) propellent gases,
and mixtures thereof.

The compositions according to the invention have, for example, an oil or fat component B) which is chosen from: hydrocarbons of low polarity, such as mineral oils; linear saturated hydrocarbons, preferably having more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example under the name cyclomethicone.

Preferred oil and fat components B) are chosen from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti, and mixtures of the abovementioned oil and fat components.

Suitable cosmetically and pharmaceutically compatible oil and fat components B) are described in Karl-Heinz Schrader, Grundlagen and Rezepturen der Kosmetika [Fundamentals and formulations of cosmetics], 2nd Edition, Verlag Hüthig, Heidelberg, pp. 319-355, to which reference is hereby made.

Suitable hydrophilic carriers B) are chosen from water, mono-, di- or polyhydric alcohols having preferably 1 to 8 carbon atoms, such as ethanol, n-propanol, isopropanol, propylene glycol, glycerol, sorbitol, etc.

In one embodiment according to the invention, the compositions comprise 20% by weight or more of water.

In a further embodiment according to the invention, the compositions comprise less than 20% by weight, preferably less than 10% by weight, particularly preferably less than 5% by weight, of water.

A suitable propellent gas B) is propane/butane.

The cosmetic compositions according to the invention may be skin cosmetic, hair cosmetic, dermatological, hygiene or pharmaceutical compositions. On account of their film-forming properties, the above-described copolymers and polyelectrolyte complexes are suitable in particular as additives for hair and skin cosmetics.

Preferably, the compositions according to the invention are in the form of a gel, foam, spray, ointment, cream, emulsion, suspension, lotion, milk or paste. If desired, it is also possible to use liposomes or microspheres.

The cosmetically or pharmaceutically active compositions according to the invention can additionally comprise cosmetically and/or dermatologically active ingredients, and auxiliaries.

Preferably, the cosmetic compositions according to the invention comprise at least one copolymer A) as defined above, at least one carrier B) as defined above and at least one constituent different therefrom which is chosen from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tints, tanning agents, dyes, pigments, consistency regulators, humectants, refatting agents, collagen, protein hydrolyzates, lipids, antioxidants, antifoams, antistats, emollients and softeners.

Customary thickeners in such formulations are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Preference is given to using nonionic thickeners.

Suitable cosmetically and/or dermatologically active ingredients are, for example, coloring active ingredients, skin and hair pigmentation agents, tints, tanning agents, bleaches, keratin-hardening substances, antimicrobial active ingredients, photo filter active ingredients, repellent active ingredients, hyperemic substances, keratolytic and keratoplastic substances, antidandruff active ingredients, antiphlogistics, keratinizing substances, antioxidative active ingredients and active ingredients which act as free-radical scavengers, skin-moisturizing or humectant substances, refatting active ingredients, antierythimatous or antiallergic active ingredients and mixtures thereof.

Artificially skin-tanning active ingredients which are suitable for tanning the skin without natural or artificial irradiation with UV rays are, for example, dihydroxyacetone, alloxan and walnut shell extract. Suitable keratin-hardening substances are generally active ingredients as are also used in antiperspirants, such as, for example, potassium aluminum sulfate, aluminum hydroxychloride, aluminum lactate, etc. Antimicrobial active ingredients are used to destroy microorganisms or to inhibit their growth and thus serve both as preservative and also as deodorizing substance which reduces the formation or the intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable photofilter active ingredients are substances which absorb UV rays in the UV-B and/or UV-A region. Suitable UV filters are, for example, 2,4,6-triaryl-1,3,5-triazines in which the aryl groups can in each case carry at least one substituent which is preferably chosen from hydroxy, alkoxy, specifically methoxy, alkoxycarbonyl, specifically methoxycarbonyl and ethoxycarbonyl and mixtures thereof. Also suitable are p-aminobenzoic esters, cinnamic esters, benzophenones, camphor derivatives, and pigments which stop UV rays, such as titanium dioxide, talc and zinc oxide. Suitable repellent active ingredients are compounds which are able to keep off or drive off certain animals, in particular insects, from people. These include, for example, 2-ethyl-1,3-hexanediol, N,N-diethyl-m-toluamide etc. Suitable hyperemic substances, which stimulate blood flow through the skin, are, for example, essential oils, such as dwarf pine, lavender, rosemary, juniper berry, horsechestnut extract, birch leaf extract, hayflower extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counteract skin irritations, are, for example, allantoin, bisabolol, dragosantol, camomile extract, panthenol, etc.

The compositions according to the invention can comprise, as active ingredient, e.g. as cosmetic and/or pharmaceutical active ingredient, at least one polymer which differs from the copolymers A) according to the invention. These include, quite generally, anionic, cationic, amphoteric and neutral polymers.

Examples of anionic polymers are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and, optionally, further vinyl esters (e.g. Luviset® grades), maleic anhydride copolymers, optionally reacted with alcohol, anionic polysiloxanes, e.g. carboxy-functional carboxypolysiloxanes, copolymers of vinylpyrrolidone, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of (meth)acrylic acid, $C_4$-$C_{30}$-alkylvinyl esters, $C_4$-$C_{30}$-alkyl vinyl ethers and hyaluronic acid. Examples of anionic polymers are also vinyl acetate/crotonic acid copolymers, as are commercially available, for example, under the names Resyn® (National Starch) and Gafset® (GAF) and vinylpyrrolidone/vinyl acrylate copolymers obtainable, for example, under the trade name Luviflex® (BASF). Further suitable polymers are vinylpyrrolidone/acrylate terpolymers available under the name Luviflex® VBM-35 (BASF), and polyamides containing sodium sulfonate or polyesters containing sodium sulfonate. Also suitable are vinylpyrrolidone/ethyl methacrylate/methacrylic acid copolymers, as are sold by Stepan under the names Stepanhold-Extra and -R1, and the Carboset® grades from BF Goodrich.

Suitable cationic polymers are, for example, cationic polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by reacting polyvinylpyrrolidone with quaternary ammonium compounds), polymer JR (hydroxyethylcellulose with cationic groups) and plant-based cationic polymers, e.g. guar polymers, such as the Jaguar® grades from Rhodia. Also suitable are cationic polyurethanes, e.g. those described in WO 2006/069742.

Very particularly suitable polymers are neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially hydrolyzed copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers available under the names Amphomer® (National Starch), and zwitterionic polymers, as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyether siloxanes, such as Tegopren® (Goldschmidt) or Belsil® (Wacker).

The formulation basis of pharmaceutical compositions according to the invention preferably comprises pharmaceutically acceptable auxiliaries. Of pharmaceutical acceptability are the auxiliaries which are known for use in the field of pharmacy, food technology and related fields, in particular the auxiliaries listed in relevant pharmacopoeia (e.g. DAB Ph. Eur. BP NF), and other auxiliaries whose properties do not preclude a physiological application.

Suitable auxiliaries may be: glidants, wetting agents, emulsifying and suspending agents, preservatives, antioxidants, antiirritative substances, chelating agents, emulsion stabilizers, film formers, gel formers, odor masking agents, resins, hydrocolloids, solvents, solubility promoters, neutralizing agents, permeation accelerators, pigments, quaternary ammonium compounds, refatting and superfatting agents, ointment, cream or oil base substances, silicone derivatives, stabilizers, sterilizing agents, propellants, drying agents, opacifiers, thickeners, waxes, softeners, white oils. One embodiment with regard to this is based on expert knowledge, as given, for example, in Fiedler, H. P. Lexikon der Hilfsstoffe für Pharmazie, Kosmetik and angrenzende Gebiete [Lexicon of the auxiliaries for pharmacy, cosmetics and related fields], 4th Edition, Aulendorf: ECV-Editio-Kantor Verlag, 1996.

To prepare the dermatological compositions according to the invention, the active ingredients can be mixed or diluted with a suitable auxiliary (excipient). Excipients may be solid, semisolid or liquid materials which can serve as vehicles, carriers or medium for the active ingredient. The admixing of further auxiliaries takes place, if desired, in the manner known to the person skilled in the art. In addition, the polymers and polyelectrolyte complexes are suitable as auxiliaries in pharmacy, preferably as or in (a) coating(s) or (a) binder(s) for solid drug forms. They can also be used in creams and as tablet coatings and tablet binders.

According to a preferred embodiment, the compositions according to the invention are skin-cleansing compositions.

Preferred skin-cleansing compositions are soaps of liquid to gel consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and gels, foam baths, oil baths and scrub preparations, shaving foams, lotions and creams.

According to a further preferred embodiment, the compositions according to the invention are cosmetic compositions for the care and protection of the skin, nailcare compositions or preparations for decorative cosmetics.

Suitable skin cosmetic compositions are, for example, face tonics, face masks, deodorants and other cosmetic lotions. Compositions for use in decorative cosmetics include, for example, concealing sticks, stage make-up, mascara and eyeshadows, lipsticks, kohl pencils, eyeliners, blushers, powder and eyebrow pencils.

Furthermore, the ampholytic copolymers can be used in nose strips for pore cleansing, in antiacne compositions, repellents, shaving compositions, hair removal compositions, intimate care compositions, footcare compositions, and in babycare.

The skincare compositions according to the invention are, in particular, W/O or O/W skin creams, day and night creams, eye creams, face creams, antiwrinkle creams, moisturizing creams, bleach creams, vitamin creams, skin lotions, care lotions and moisturizing lotions.

Skin cosmetic and dermatological compositions based on the above-described ampholytic copolymers exhibit advantageous effects. The polymers can, inter alia, contribute to the moisturization and conditioning of the skin and to an improvement in the feel of the skin. The polymers can also act as thickeners in the formulations. By adding the polymers according to the invention, a considerable improvement in skin compatibility can be achieved in certain formulations.

Skin cosmetic and dermatological compositions preferably comprise at least one ampholytic copolymer in an amount of from about 0.001 to 30% by weight, preferably 0.01 to 20% by weight, very particularly preferably 0.1 to 12% by weight, based on the total weight of the composition.

Particularly photoprotective agents based on the ampholytic copolymers have the property of increasing the residence time of the UV-absorbing ingredients compared to customary auxiliaries such as polyvinylpyrrolidone.

Depending on the field of use, the compositions according to the invention can be applied in a form suitable for skincare, such as, for example, as cream, foam, gel, stick, mousse, milk, spray (pump spray or propellent-containing spray) or lotion.

Besides the ampholytic copolymers and suitable carriers, the skin cosmetic preparations can also comprise further active ingredients customary in skin cosmetics and auxiliaries as described above. These include, preferably, emulsifiers, preservatives, perfume oils, cosmetic active ingredients such as phytantriol, vitamin A, E and C, retinol, bisabolol, panthenol, photoprotective agents, bleaches, colorants, tints, tanning agents, collagen, protein hydrolyzates, stabilizers, pH regulators, dyes, salts, thickeners, gel formers, consistency regulators, silicones, humectants, refatting agents and further customary additives.

Preferred oil and fat components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$ fatty acids, wax esters, such as, for example, jojoba oil, fatty alcohols, vaseline, hydrogenated lanolin and acetylated lanolin, and mixtures thereof.

The ampholytic copolymers according to the invention can also be mixed with conventional polymers if specific properties are to be set.

To set certain properties, such as, for example, improve the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are prepared by customary methods known to the person skilled in the art.

Preferably, the cosmetic and dermatological compositions are in the form of emulsions, in particular as water-in-oil (W/O) or oil-in-water (O/W) emulsions. However, it is also possible to choose other types of formulation, for example hydrodispersions, gels, oils, oleogels, multiple emulsions, for example in the form of W/O/W or O/W/O emulsions, anhydrous ointments or ointment bases, etc.

Emulsions are prepared by known methods. Besides at least one ampholytic copolymer, the emulsions usually comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The selection of additives specific to the type of emulsion and the preparation of suitable emulsions is described, for example, in Schrader, Grundlagen and Rezepturen der Kosmetika [Fundamentals and formulations of cosmetics], Hüthig Buch Verlag, Heidelberg, 2nd Edition, 1989, third part, to which reference is hereby expressly made.

A suitable emulsion, e.g. for a skin cream etc., generally comprises an aqueous phase which is emulsified by means of a suitable emulsifier system in an oil or fatty phase. To provide the aqueous phase, an ampholytic copolymer according to the invention can be used.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karité oil, hoplostethus oil; mineral oils whose distillation start-point under atmospheric pressure is at about 250° C. and whose distillation end-point is at 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase can also comprise silicone oils soluble in other oils, such as dimethylpolysiloxane, methylphenylpolysiloxane and the silicone glycol copolymer, fatty acids and fatty alcohols.

Besides the ampholytic copolymers, it is also possible to use waxes, such as, for example, carnauba wax, candelilla wax, beeswax, microcrystalline wax, ozokerite wax and Ca, Mg and Al oleates, myristates, linoleates and stearates.

Furthermore, an emulsion according to the invention can be in the form of an O/W emulsion. Such an emulsion usually comprises an oil phase, emulsifiers which stabilize the oil phase in the water phase, and an aqueous phase which is usually in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bath preparation.

Such formulations comprise at least one ampholytic copolymer and usually anionic surfactants as base surfactants and amphoteric and/or nonionic surfactants as cosurfactants. Further suitable active ingredients and/or auxiliaries are usually chosen from lipids, perfume oils, dyes, organic acids, preservatives and antioxidants, and thickeners/gel formers, skin conditioners and humectants.

These formulations comprise preferably 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleaning compositions can be used in the washing, shower and bath preparations. Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or am phodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

Furthermore, the washing, shower and bath preparations can comprise customary cationic surfactants, such as, for example, quaternary ammonium compounds, for example cetyltrimethylammonium chloride.

In addition, the shower gel/shampoo formulations can comprise thickeners, such as, for example, sodium chloride, PEG-55, propylene glycol oleate, PEG-120 methylglucose dioleate and others, and preservatives, further active ingredients and auxiliaries and water.

According to a particularly preferred embodiment, the compositions according to the invention are hair-treatment compositions.

Hair-treatment compositions according to the invention comprise preferably at least one ampholytic copolymer in an amount in the range from about 0.1 to 30% by weight, preferably 0.5 to 20% by weight, based on the total weight of the composition.

Preferably, the hair-treatment compositions according to the invention are in the form of a hairspray, setting foam, hair mousse, hair gel, shampoo, hair foam, end fluid, neutralizer for permanent waves, hair colorant and bleach or hot-oil treatment. Depending on the field of use, the hair cosmetic preparations can be applied as (aerosol) spray, (aerosol) foam, mousse, gel, gel spray, cream, lotion or wax. Hairsprays here comprise both aerosol sprays and pump sprays without propellent gas. Hair foams comprise both aerosol foams and also pump foams without propellent gas. Hairsprays and hair foams comprise preferably predominantly or exclusively water-soluble or water-dispersible components. If the compounds used in the hairsprays and hair foams according to the invention are water-dispersible, they can be used in the form of aqueous microdispersions with particle diameters of from usually 1 to 350 nm, preferably 1 to 250 nm. The solids contents of these preparations are usually in a range from about 0.5 to 20% by weight. These microdispersions generally require no emulsifiers or surfactants for their stabilization.

Copolymers which comprise 0.01 to 3% by weight of at least one compound f) in copolymerized form are particularly suitable as setting agents and/or conditioners in hair-treatment compositions. Likewise, copolymers which have a K value of 42 or more are particularly suitable as setting agents and/or conditioners in hair-treatment compositions. These hair-treatment compositions are selected from hair gel, shampoo, setting foam, hair tonic, hair spray, hair foam or mousse.

In one preferred embodiment, the hair cosmetic formulations according to the invention comprise
  a) 0.05 to 20% by weight of at least one ampholytic copolymer, as defined above,
  b) 20 to 99.95% by weight of water and/or alcohol,
  c) 0 to 50% by weight of at least one propellent gas,
  d) 0 to 5% by weight of at least one emulsifier,
  e) 0 to 3% by weight of at least one thickener, and
  f) up to 25% by weight of further constituents.

Alcohol is to be understood as meaning all alcohols customary in cosmetics, e.g. ethanol, isopropanol, n-propanol.

Further constituents are to be understood as meaning the additives customary in cosmetics, for example propellents, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances such as panthenol, collagen, vitamins, protein hydrolyzates, alpha- and beta-hydroxycarboxylic acids, protein hydrolyzates, stabilizers, pH regulators, dyes, viscosity regulators, gel formers, dyes, salts, humectants, refatting agents, complexing agents and further customary additives.

These also include all styling and conditioner polymers known in cosmetics which can be used in combination with the polymers according to the invention if very specific properties are to be set.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and amino-functional silicone compounds such as amodimethicones (CTFA).

The ampholytic copolymers and polyelectrolyte complexes according to the invention are suitable in particular as setting agents in hairstyling preparations, in particular hairsprays (aerosol sprays and pump sprays without propellent gas) and hair foams (aerosol foams and pump foams without propellent gas).

In one preferred embodiment, spray preparations comprise
  a) 0.1 to 10% by weight of at least one ampholytic copolymer, as defined above,
  b) 20 to 94.9% by weight of water and/or alcohol,
  c) 0 to 70% by weight of at least one propellent,
  d) 0 to 20% by weight of further constituents.

Propellents are the propellents used customarily for hairsprays or aerosol foams. Preference is given to mixtures of propane/butane, pentane, dimethyl ether, 1,1-difluoroethane (HFC-152 a), carbon dioxide, nitrogen or compressed air.

A formulation preferred according to the invention for aerosol hair foams comprises
  a) 0.1 to 10% by weight of at least one ampholytic copolymer, as defined above,
  b) 55 to 94.8% by weight of water and/or alcohol,
  c) 5 to 20% by weight of a propellent,
  d) 0.1 to 5% by weight of an emulsifier,
  e) 0 to 10% by weight of further constituents.

Emulsifiers which can be used are all emulsifiers used customarily in hair foams. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether; cetearetes, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methylsulfate, quaternium-1 to x (INCI).

Anionic emulsifiers can be chosen, for example, from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition:
  a) 0.1 to 10% by weight of at least one ampholytic copolymer, as defined above,
  b) 80 to 99.9% by weight of water and/or alcohol,
  c) 0 to 3% by weight, preferably 0.05 to 2% by weight, of a gel former,
  d) 0 to 20% by weight of further constituents.

In general, the copolymers according to the invention already have a "self-thickening" effect, meaning that, during the production of gels, the use of gel formers can in many cases be dispensed with. However, its use may be advantageous in order to establish specific rheological or other application-related properties of the gels. Gel formers which may be used are all gel formers customary in cosmetics. These include slightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) paraffinum liquidum (INCI), sodium acrylate copolymers (and) paraffinum liquidum (and) PPG-1 trideceth-6, acrylamidopropyltrimonium chloride/acrylamide copolymers, steareth-10 allyl ether acrylate copolymers, polyquaternium-37 (and) paraffinum liquidum (and) PPG-1 trideceth-6, polyquaternium 37 (and) propylene glycol dicaprate dicaprylate (and) PPG-1 trideceth-6, polyquaternium-7, polyquaternium-44.

Copolymers which comprise 0.01 to 3% by weight of at least one compound f) in copolymerized form are particularly suitable as rheology modifiers in skin cleansing compositions, compositions for the care and protection of the skin, nailcare compositions, preparations for decorative cosmetics and hair treatment composition.

The ampholytic copolymers according to the invention can be used in cosmetic preparations as conditioners.

The ampholytic copolymers according to the invention as defined above can preferably be used in shampoo formulations as setting agents and/or conditioners. Preferred shampoo formulations comprise a) 0.05 to 10% by weight of at least one ampholytic copolymer, as defined above,
b) 25 to 94.95% by weight of water,
c) 5 to 50% by weight of surfactants,
d) 0 to 5% by weight of a further conditioner,
e) 0 to 10% by weight of further cosmetic constituents.

In the shampoo formulations, all anionic, neutral, amphoteric or cationic surfactants used customarily in shampoos can be used.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Of suitability are, for example, sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkylamine oxides, mono- or dialkylalkanolamides, fatty acid esters of polyethylene glycols, alkyl polyglycosides or sorbitan ether esters.

Furthermore, the shampoo formulations can comprise customary cationic surfactants, such as, for example, quaternary ammonium compounds, for example cetyltrimethylammonium chloride.

In the shampoo formulations, in order to achieve certain effects, customary conditioners can be used in combination with the ampholytic copolymers. These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). It is also possible to use protein hydrolyzates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and amino-functional silicone compounds, such as amodimethicones (CTFA). It is also possible to use cationic guar derivatives, such as guar hydroxypropyltrimonium chloride (INCI).

The invention further provides the use of an ampholytic copolymer, as auxiliary in pharmacy, preferably as or in coating(s) for solid drug forms, for modifying rheological properties, as surface-active compound, as or in adhesive(s), and as or in coating(s) for the textile, paper, printing and leather industries.

The invention is explained in more detail by reference to the following nonlimiting examples.

EXAMPLES

General Preparation Procedure

Example 6

TBA/VP/DMAPMAM/quat
DMAEMA/MAA=47:25:5:20:3

| Initial charge | 73 g | Water |
|---|---|---|
|  | 112 g | Ethanol |
|  | 23 g | Feed 1 |
|  | 26 g | Feed 2 |
| Feed 1 | 225 g | tert-Butyl acrylate |
|  | 120 g | Vinylpyrrolidone |
|  | 24 g | N,N-Dimethylaminopropylmethacrylamide |
|  | 174 g | 50% strength Quat 311 solution |
|  | 14.4 g | Methacrylic acid |
|  | 100 g | Ethanol |
| Feed 2 | 150 g | Water |
|  | 300 g | Ethanol |
|  | 0.96 g | tert-Butyl perpivalate 75% strength |
| Feed 3 | 150 g | Water |
|  | 300 g | Ethanol |
|  | 2 g | tert-Butyl perpivalate 75% strength |
| Feed 4 | 480 g | Ethanol |

The initial charge was heated to about 70° C. with stirring in a stirred apparatus with reflux condenser, internal thermometer and four separate feed devices. Following the onset of polymerization, recognizable from a slight increase in viscosity, at 70° C., the remainder of feed 1 was added over the course of 3 hours and the remainder of feed 2 was added over the course of 4 hours. The reaction solution was then stirred for about a further 2 hours at 70° C. Feed 3 was metered in at about 80° C. over 15 minutes and the polymer mixture was stirred for about another 4 hours at 80° C. After cooling to about 60° C., the pH was adjusted to 5.9 with phosphoric acid. Then, at an external temperature of 120° C., ethanol was removed from the reaction solution by steam distillation. The polymer solution was cooled to about 40° C., diluted with ethanol (feed 4) and adjusted to a solids content of 30% with water. The polymers in table 1 below were prepared analogously.

TABLE 1

| Ex. No. | TBA | VP | DMAPMAM | DMAEMA | quat DMAEMA | MAA | Neutralizing agent/ $N_d$ or pH | K value |
|---|---|---|---|---|---|---|---|---|
| 1 | 55 | 27 | | 10 | 5 | 3 | H₃PO₄ 60% | 19 |
| 2 | 50 | 25 | 18 | | 5 | 2 | H₃PO₄ pH 5.9 | 34.1 |
| 3 | 50 | 25 | 20 | | 3 | 2 | H₃PO₄ pH 6.3 | 34.4 |
| 4 | 50 | 27 | | 15 | 5 | 3 | Lactic acid 90% | 25.1 |
| 5 | 47 | 25 | 10 | | 15 | 3 | H₃PO₄ pH 6.1 | 45 |
| 6 | 47 | 25 | 5 | | 20 | 3 | H₃PO₄ pH 5.9 | 41.8 |
| 7 | 45 | 30 | 15 | | 3 | 7 | Lactic acid 90% | 33.9 |
| 8 | 45 | 30 | | 17 | 5 | 3 | H₃PO₄ 50% | 39.8 |
| 9 | 45 | 30 | 18 | | 4 | 3 | H₃PO₄ 50% | 43.7 |
| 10 | 45 | 30 | | 18 | 5 | 2 | H₃PO₄ 50% | 44.4 |
| 11 | 45 | 30 | 18 | | 5 | 2 | H₃PO₄ 50% | 36.7 |
| 12 | 45 | 25 | 15 | | 10 | 5 | H₃PO₄ pH 5.9 | 41.6 |
| 13 | 42 | 30 | 10 | | 15 | 3 | H₃PO₄ pH 5.9 | 39.9 |
| 14 | 42 | 30 | 5 | | 20 | 3 | H₃PO₄ pH 5.9 | 38.6 |
| 15 | 42 | 35 | 4 | | 17 | 2 | H₃PO₄ pH 5.7 | 39.8 |
| 16 | 42 | 30 | | | 25 | 3 | H₃PO₄ pH 5.0 | 37.5 |
| 17 | 37 | 35 | 10 | | 15 | 3 | H₃PO₄ pH 5.9 | 39.8 |
| 18 | 37 | 35 | 5 | | 20 | 3 | H₃PO₄ pH 6.0 | 40.6 |
| 19 | 37 | 40 | 4 | | 17 | 2 | H₃PO₄ pH 6.1 | 41.5 |
| 20 | 37 | 35 | | | 25 | 3 | H₃PO₄ pH 5.4 | 37.3 |

TBA tert-butyl acrylate
VP vinylpyrrolidone
DMAPMAM dimethylaminopropylmethacrylamide
DMAEMA dimethylaminoethyl methacrylate
quat. DMAEMA dimethylaminoethyl methacrylate quaternized with diethyl sulfate
MAA methacrylic acid
$N_d$ degree of neutralization in %
K value 1% strength in N-methylpyrrolidone Example 21

TBA/VP/DMAPMAM/Q311/MAA/EGDMA=35/37/10/15/3/0.1 ppH

| Initial charge | 100 g | Water |
|---|---|---|
| | 50 g | Isopropanol |
| | 45 g | Feed 1 |
| | 2.5 g | Feed 2 |
| Feed 1 | 164.6 g | tert-Butyl acrylate |
| | 174 g | Vinylpyrrolidone |
| | 47 g | N,N-dimethylaminopropylmethacrylamide |
| | 140.8 g | 50% strength Quat 311 solution |
| | 14.4 g | Methacrylic acid |
| | 0.5 g | Ethylene glycol dimethacrylate |
| | 250 g | Isopropanol |
| | 130 g | Water |
| Feed 2 | 50 g | Isopropanol |
| | 0.8 g | tert-Butyl perpivalate 75% strength |
| Feed 3 | 50 g | Water |
| | 70 g | Isopropanol |
| | 0.6 g | tert-Butyl perpivalate 75% strength |

The initial charge was heated to about 70° C. with stirring in a stirred apparatus with reflux condenser, internal thermometer and three separate feed devices. Following the onset of polymerization, recognizable from a slight increase in viscosity, at 70° C., the remainder of feed 1 was added over the course of three hours and the remainder of feed 2 was added over the course of four hours. The reaction solution was then stirred for about a further two hours at 70° C. Feed 3 was metered in at about 80° C. over 15 minutes and the polymer mixture was stirred for about another four hours at 80° C. After cooling to about 60° C., the pH was adjusted to 5.9 with phosphoric acid. Then, at an external temperature of 120° C., isopropanol was removed from the reaction solution by steam distillation. The polymer solution was cooled to about 40° C. and adjusted to a solids content of 20% with water. The polymers in table 2 below were prepared analogously.

TABLE 2

| Ex. No. | TBA | VP | DMAPMAM | quat DMAEMA | MAA | Cross-linker | Neutralizing agent/ pH | K value |
|---|---|---|---|---|---|---|---|---|
| 21 | 35 | 37 | 10 | 15 | 3 | EGDMA 0.1 ppH | $H_3PO_4$ pH 5.8 | 48.7 |
| 22 | 30 | 45 | 10 | 13 | 2 | EGDMA 0.2 ppH | $H_3PO_4$ pH 5.5 | 53.3 |
| 23 | 42 | 30 | 10 | 15 | 3 | PETAE 0.1 ppH | $H_3PO_4$ pH 5.8 | 47.6 |
| 24 | 35 | 37 | 10 | 15 | 3 | PETAE 0.1 ppH | $H_3PO_4$ pH 5.6 | 40.1 |

TBA tert-Butyl acrylate
VP vinylpyrrolidone
DMAPMAM dimethylaminopropylmethacrylamide
quat. DMAEMA dimethylaminoethyl methacrylate quaternized with diethyl sulfate
MAA methacrylic acid
K value 1% strength in N-nethylpyrrolidone
EGDMA: ethylene glycol dimethacrylate
PETAE: pentaerythritol triallyl ether
ppH parts per 100 parts of monomer

Application Examples

Unless indicated otherwise, parts are parts by weight.
A) Copolymers without Compound f)
I) Use in Hair Cosmetics:
  1) VOC 80 Aerosol Hairspray (Example Nos. 1-20)

| | |
|---|---|
| Polymer 1, 2, 3, 4, 5, 6, 7, 8, 9, 10, 11, 12, 13, 14, 15, 16, 17, 18, 19, 20 (30% strength aqueous-ethanol. solution) | 10.0 |
| Water | 13.0 |
| Dimethyl ether | 40.0 |
| Ethanol | 37.0 |

Further Additives:
  Preservative, soluble ethoxylated silicone, perfume, antifoam . . . .
  2) VOC 80 Aerosol Hairspray (Example Nos. 21-40)
  3% polymer according to the invention+1% Luviskol® VA 64

| | |
|---|---|
| Polymer 1, 2, 3, 4, 5, 6, 7, 8, 9, 10, 11, 12, 13, 14, 15, 16, 17, 18, 19, 20 (30% strength aqueous-ethanol. solution) | 10.0 (3.0 polymer + 7.0 ethanol) |
| Luviskol ® VA 64 (powder) | 1.0 |
| Water | 12.0 |
| Dimethyl ether | 40.0 |
| Ethanol | 37.0 |

Further Additives:
  Preservative, soluble ethoxylated silicone, perfume, antifoam . . . .
  3) VOC 55 Aerosol Hairspray (Example Nos. 41-60)

| | |
|---|---|
| Polymer 1, 2, 3, 4, 5, 6, 7, 8, 9, 10, 11, 12, 13, 14, 15, 16, 17, 18, 19, 20 (30% strength aqueous-ethanol, solution) | 8.75 |
| Water | 38.75 |
| Dimethyl ether | 40.0 |
| Ethanol | 12.5 |

Further Additives:
  Preservative, soluble ethoxylated silicone, perfume, antifoam . . . .
  4) VOC 55 Aerosol Hairspray (Example Nos. 61-80)
  3% polymer according to the invention+1% Luviskol® VA 64

| | |
|---|---|
| Polymer 1, 2, 3, 4, 5, 6, 7, 8, 9, 10, 11, 12, 13, 14, 15, 16, 17, 18, 19, 20 (30% strength aqueous-ethanol. solution) | 10.0 |
| Luviskol ® Plus | 1.0 |
| Water | 37.0 |
| Dimethyl ether | 40.0 |
| Ethanol | 12.0 |

Further Additives:
  Preservative, soluble ethoxylated silicone, perfume, antifoam . . . .
  5) VOC 55 Pump Spray (Example Nos. 81-100)

| | |
|---|---|
| Polymer 1, 2, 3, 4, 5, 6, 7, 8, 9, 10, 11, 12, 13, 14, 15, 16, 17, 18, 19, 20 (30% strength aqueous-ethanol. solution) | 10.0 |
| Water | 37.0 |
| Ethanol | 53.0 |

Further Additives:
Preservative, soluble ethoxylated silicone, perfume, antifoam . . . .

6) Setting Foam (Example Nos. 101-120)

| | | |
|---|---|---|
| Polymer 1, 2, 3, 4, 5, 6, 7, 8, 9, 10, 11, 12, 13, 14, 15, 16, 17, 18, 19, 20 (30% strength aqueous-ethanol, solution) | 6.6 | |
| Cremophor ® A 25 | 0.25 | (Ceteareth 25, BASF) |
| Comperlan ® KD | 0.15 | (Coamide DEA, Henkel) |
| Water | 80.0 | |
| Dimethyl ether | 10.0 | |

Further additives: perfume, preservative . . . .
Preparation: Weigh in and dissolve with stirring. Bottle and add propellant gas.

7) Shampoo (Examples 121-140)

| | CTFA | % by wt. |
|---|---|---|
| Phase 1: | | |
| Polymer from Example No. 1, 2, 3,4, 5, 6, 7, 8, 9, 10, 11, 12, 13, 14, 15, 16, 17, 18, 19, 20 | | 1.0 |
| Water adjust to pH 6.5 with triethanolamine (50% strength) | | 48.0 |
| Phase 2: | | |
| Texapon ® NSO 28% strength | Sodium Laureth Sulfphate/Henkel | 50.0 |
| Coperlan ® KD | Coamide DEA/Henkel | 1.0 |

Further additive: perfume, preservative, etc.
Preparation:
Weigh in and dissolve phases 1 and 2 separately with stirring and mix. Slowly stir phase 2 into phase 1.

8) Anhydrous Hair Spray (Example Nos. 141-160)

| | |
|---|---|
| Polymer 1, 2, 3, 4, 5, 6, 7, 8, 9, 10, 11, 12, 13, 14, 15, 16, 17, 18, 19, 20 (dried product, 100%) | 3.0 |
| Propane/butane | 40.0 |
| Ethanol | 57.0 |

Further Additives:
Preservative, soluble ethoxylated silicone, perfume, antifoam . . . .

9) Anhydrous Hair Spray (Example Nos. 161-180)
2% polymer according to the invention+1% Luviskol® Plus

| | |
|---|---|
| Polymer 1, 2, 3, 4, 5, 6, 7, 8, 9, 10, 11, 12, 13, 14, 15, 16, 17, 18, 19, 20 | 2.0 |
| (dried product, 100%) | |
| Luviskol ® Plus | 1.0 |
| Propane/butane | 40.0 |
| Ethanol | 57.0 |

Further Additives:
Preservative, soluble ethoxylated silicone, perfume, antifoam . . . .

II) Use in Skin Cosmetics:

10) Standard O/W Cream (Example Nos. 181-200)

| | % | CTFA Name |
|---|---|---|
| Oil phase: | | |
| Cremophor ® A6 | 3.5 | Ceteareth-6 (and) stearyl alcohol |
| Cremophor ® A25 | 3.5 | Ceteareth-25 |
| Glycerol monostearate | 2.5 | Glyceryl stearate |
| Paraffin oil | 7.5 | Paraffin oil |
| Cetyl alcohol | 2.5 | Cetyl alcohol |
| Luvitol ® EHO | 3.2 | Cetearyl octanoate |
| Vitamin E acetate | 1.0 | Tocopheryl acetate |
| Nip-Nip | 0.1 | Methyl and propyl 4-hydroxy-benzoate (7:3) |
| Water phase: | | |
| Polymer 1, 2, 3, 4, 5, 6, 7, 8, 9, 10, 11, 12, 13, 14, 15, 16, 17, 18, 19, 20 (30% strength aqueous-ethanol. solution) | 3.0 | |
| Water | 74.6 | |
| 1,2-Propylene glycol | 1.5 | Propylene glycol |
| Germall II | 0.1 | Imidazolidinylurea |

Preparation: The components are weighed in and the oil phase and water phase are homogenized separately with stirring at a temperature of about 80° C. The water phase is slowly stirred into the oil phase and the mixture is cooled to room temperature with stirring.

11) Day Lotion (Example Nos. 201-220)

| | % | CTFA Name |
|---|---|---|
| Oil phase: | | |
| Cremophor ® A6 | 1.5 | Ceteareth-6 (and) stearyl alcohol |
| Cremophor ® A25 | 1.5 | Ceteareth-25 |
| Glycerol monostearate | 5.0 | Glyceryl stearate |
| Uvinul ® MS 40 | 0.5 | Bezophenone-4 |
| Paraffin oil | 3.5 | Paraffin oil |
| Cetyl alcohol | 0.5 | Cetyl alcohol |
| Luvitol ® EHO | 10.0 | Cetearyl octanoate |
| D-Panthenol 50 P | 3.0 | Panthenol and propylene glycol |
| Vitamin E acetate | 1.0 | Tocopheryl acetate |
| Tegiloxan 100 | 0.3 | Dimethicone |
| Nip-Nip | 0.1 | Methyl and propyl 4-hydroxy-benzoate (7:3) |
| Water phase: | | |
| Polymer 1, 2, 3, 4, 5, 6, 7, 8, 9, 10, 11, 12, 13, 14, 15, 16, 17, 18, 19, 20 (30% strength aqueous-ethanol. solution) | 1.5 | |
| Water | 70.0 | |
| 1,2-Propylene glycol | 1.5 | Propylene glycol |
| Germall II | 0.1 | Imidazolidinylurea |

Preparation: The components are weighed in and the oil phase and water phase are homogenized separately with stirring at a temperature of about 80° C. The water phase is slowly stirred into the oil phase and the mixture is cooled to room temperature with stirring.

B) Copolymers with Compound f)

I) Use in Hair Cosmetics:

12) Setting Foam (Example Nos. 221-224)

| | | |
|---|---|---|
| Polymer 21, 22, 23, 24 | 10.0 | |
| (20% strength aqueous solution) | | |
| Cremophor ® A 25 | 0.25 | (Ceteareth 25, BASF) |
| Comperlan ® KD | 0.15 | (Coamide DEA, Henkel) |
| Water | 79.6 | |
| Dimethyl ether | 10.0 | |

Further additives: Perfume, preservative . . . .

Preparation: Weigh and dissolve with stirring. Bottle and add propellent gas.

13) Liquid Hair Gel (Example Nos. 225-228)

| | | |
|---|---|---|
| Natrosol ® 250 HR | 4.0 | (hydroxyethylcellulose) |
| Water | 64.0 | |
| Polymer 21, 22, 23, 24 | 10.0 | |
| (20% strength aqueous solution) | | |
| Water | 20.0 | |
| Glycerol | 2.0 | |

Further additives: Perfume, preservative . . . .

Preparation: Weigh Natrosol into water and dissolve with stirring. Polymer/glycerol solution is prepared separately, then stirred slowly into Natrosol solution.

II) Use in Skin Cosmetics:

14) Standard O/W Cream (Example Nos. 229-232)

| | % | CTFA Name |
|---|---|---|
| Oil phase: | | |
| Cremophor ® A6 | 3.5 | Ceteareth-6 (and) stearyl Alcohol |
| Cremophor ® A25 | 3.5 | Ceteareth-25 |
| Glycerol monostearate | 2.5 | Glyceryl stearate |
| Paraffin oil | 7.5 | Paraffin oil |
| Cetyl alcohol | 2.5 | Cetyl alcohol |
| Luvitol ® EHO | 3.2 | Cetearyl octanoate |
| Vitamin E acetate | 1.0 | Tocopheryl acetate |
| Nip-Nip | 0.1 | Methyl and propyl 4-hydroxy-benzoate (7:3) |
| Water phase: | | |
| Polymer 21, 22, 23, 24 | 3.0 | |
| (20% strength aqueous solution) | | |
| Water | 74.6 | |
| 1,2-Propylene glycol | 1.5 | Propylene glycol |
| Germall II | 0.1 | Imidazolidinylurea |

Preparation: The components are weighed in and the oil phase and water phase are homogenized separately at a temperature of about 80° C. with stirring. The water phase is slowly stirred into the oil phase and the mixture is cooled to room temperature with stirring.

15) Day Lotion (Example Nos. 233-236)

| | % | CTFA Name |
|---|---|---|
| Oil phase: | | |
| Cremophor A6 | 1.5 | Ceteareth-6 (and) stearyl alcohol |
| Cremophor A25 | 1.5 | Ceteareth-25 |
| Glycerol monostearate | 5.0 | Glyceryl stearate |
| Uvinul ® MS 40 | 0.5 | Bezophenone-4 |
| Paraffin oil | 3.5 | Paraffin oil |
| Cetyl alcohol | 0.5 | Cetyl alcohol |
| Luvitol ® EHO | 10.0 | Cetearyl octanoate |
| D-Panthenol 50 P | 3.0 | Panthenol and propylene glycol |
| Vitamin E acetate | 1.0 | Tocopheryl acetate |
| Tegiloxan 100 | 0.3 | Dimethicone |
| Nip-Nip | 0.1 | Methyl and propyl 4-hydroxy-benzoate (7:3) |
| Water phase: | | |
| Polymer 21, 22, 23, 24 | 1.5 | |
| (20% strength aqueous solution) | | |
| Water | 70.0 | |
| 1,2-Propylene glycol | 1.5 | Propylene glycol |
| Germall II | 0.1 | Imidazolidinylurea |

Preparation: The components are weighed in and the oil phase and water phase are homogenized separately at a temperature of about 80° C. with stirring. The water phase is slowly stirred into the oil phase and the mixture is cooled to room temperature with stirring.

We claim:

1. An ampholytic copolymer obtainable by free-radical polymerization of:
   a) at least one α,β-ethylenically unsaturated monomer of the general formula I

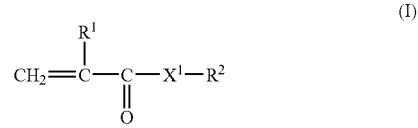

in which
   $R^1$ is hydrogen or $C_1$-$C_8$-alkyl,
   $X^1$ is O or $NR^3$, where $R^3$ is hydrogen, alkyl, cycloalkyl, aryl or hetaryl,
   $R^2$ is branched $C_3$-$C_5$-alkyl,
   b) at least one compound with a free-radically polymerizable, α,β-ethylenically unsaturated double bond and at least one cationogenic and/or cationic group per molecule which is a combination of: N-[3-(dimethylamino)propyl](meth)acrylamide and quaternized N,N-dimethylaminoethyl (meth)acrylate with the proviso that at least some of the compounds b) have at least one quaternary nitrogen atom, and 5 to 99% of monomers b) are present in quaternized form; and
   c) at least one compound with a free-radically polymerizable, α,β-ethylenically unsaturated double bond and at least one anionogenic and/or anionic group per molecule;
wherein the copolymer has a molar excess of cationogenic/cationic groups compared to anionogenic/anionic groups as characterized by a molar ratio of cationogenic/cationic groups to anionogenic/anionic groups of at least 1.01 to 1.

2. The copolymer according to claim 1, which further comprises at least one monomer d) in copolymerized form, wherein monomer d) is at least one amide-group-containing monomer which is selected from α,β-ethylenically unsaturated amide-group-containing compounds of the general formula II

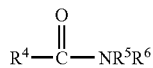

(II)

wherein
one of the radicals $R^4$ to $R^6$ is a group of the formula $CH_2=CR^7-$ where $R^7=H$ or $C_1$-$C_4$-alkyl and the other radicals $R^4$ to $R^6$, independently of one another, are H, alkyl, cycloalkyl, heterocycloalkyl, aryl or hetaryl,
$R^4$ and $R^5$, together with the amide group to which they are bonded, may also be a lactam with 5 to 8 ring atoms, and
$R^5$ and $R^6$, together with the nitrogen atom to which they are bonded, may also be a five- to seven-membered heterocycle.

3. The copolymer according to claim 1, where component a) comprises at least one monomer of the formula I in which $R^2$ is tert-butyl.

4. The copolymer according to claim 1, where component a) comprises tert-butyl acrylate or consists of tert-butyl acrylate.

5. The copolymer according to claim 1, where component c) comprises methacrylic acid or consists of methacrylic acid.

6. The copolymer according to claim 2, where component d) is selected from the group consisting of: primary amides of α,β-ethylenically unsaturated monocarboxylic acids, N-vinylamides of saturated monocarboxylic acids, N-vinyllactams, N-alkyl- and N,N-dialkylamides of α,β-ethylenically unsaturated monocarboxylic acids and mixtures thereof.

7. The copolymer according to claim 2, where component d) is selected from the group consisting of: N-vinylpyrrolidone, N-vinylcaprolactam and mixtures thereof.

8. The copolymer according to claim 1 which additionally comprises, in copolymerized form, at least one further monomer e) which is selected from the group consisting of: esters of α,β-ethylenically unsaturated mono- and dicarboxylic acids with $C_1$-$C_{30}$-alkanols, unsaturated $C_8$-$C_{30}$-fatty alcohols and $C_2$-$C_{30}$-alkanediols different from component a), amides of α,β-ethylenically unsaturated mono- and dicarboxylic acids with $C_2$-$C_{30}$-amino alcohols which have a primary or secondary amino group, esters of vinyl alcohol and allyl alcohol with $C_1$-$C_{30}$-monocarboxylic acids, vinyl ethers, vinylaromatics, vinyl halides, vinylidene halides, $C_2$-$C_8$-monoolefins, nonaromatic hydrocarbons with at least two conjugated double bonds and mixtures thereof.

9. The copolymer according to claim 2 which comprises, in copolymerized form,
20 to 94.5% by weight of at least one compound a),
5 to 79.5% by weight of at least one compound b),
0.5 to 25% by weight of at least one compound c),
0 to 74.5% by weight of at least one compound d),
0 to 25% by weight of at least one further monomer e) which is selected from the group consisting of: esters of α,β-ethylenically unsaturated mono- and dicarboxylic acids with $C_1$-$C_{30}$-alkanols, unsaturated $C_8$-$C_{30}$-fatty alcohols and $C_2$-$C_{30}$-alkanediols different from component a), amides of α,β-ethylenically unsaturated mono- and dicarboxylic acids with $C_2$-$C_{30}$-amino alcohols which have a primary or secondary amino group, esters of vinyl alcohol and allyl alcohol with $C_1$-$C_{30}$-monocarboxylic acids, vinyl ethers, vinylaromatics, vinyl halides, vinylidene halides, $C_2$-$C_8$-monoolefins, nonaromatic hydrocarbons with at least two conjugated double bonds and mixtures thereof,
0 to 5% by weight of at least one crosslinker f).

10. The copolymer according to claim 9 which comprises 0.01 to 3% by weight of at least one crosslinker f) in copolymerized form.

11. The copolymer according to claim 1 which is prepared in the presence of at least one regulator.

12. The copolymer according to claim 1 which consists of repeat units of:
tert-butyl(meth)acrylate,
at least one compound b) which is a combination of quaternized N,N-dimethylaminoethyl(meth)acrylate and N-[3-(dimethylamino)propyl](meth)acrylamide,
acrylic acid and/or methacrylic acid,
vinylpyrrolidone and/or vinylcaprolactam.

13. A cosmetic or pharmaceutical composition comprising
A) at least one ampholytic copolymer as defined in claim 1 and
B) at least one cosmetically acceptable carrier.

14. The composition according to claim 13, where component B) is selected from the group consisting of:
i) water,
ii) water-miscible organic solvents,
iii) oils, fats, waxes,
iv) esters of $C_6$-$C_{30}$-monocarboxylic acids with mono-, di- or trihydric alcohols different from iii),
v) saturated acyclic and cyclic hydrocarbons,
vi) fatty acids,
vii) fatty alcohols,
viii) propellent gases
and mixtures thereof.

15. The composition according to claim 13 which comprises propane/butane as propellant gas.

16. The composition according to claim 13 comprising at least one additive different from components A) and B) which is selected from the group consisting of: cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tints, tanning agents, dyes, pigments, consistency regulators, humectants, refatting agents, collagen, protein hydrolyzates, lipids, antioxidants, antifoams, antistats, emollients and softeners.

17. The composition according to claim 13 in the form of a spray, gel, foam, mousse, ointment, cream, emulsion, suspension, lotion, milk or paste.

18. The copolymer according to claim 1, wherein the molar ratio of cationogenic/cationic groups to anionogenic/anionic group is at least 1.2 to 1.

19. The copolymer according to claim 1, wherein the molar ratio of cationogenic/cationic groups to anionogenic/anionic group is at least 1.4 to 1.

20. The copolymer according to claim 1, wherein the molar ratio of cationogenic/cationic groups to anionogenic/anionic group is at least 1.5 to 1.

21. The copolymer according to claim 1, wherein the molar ratio of cationogenic/cationic groups to anionogenic/anionic group is at least 2 to 1.

* * * * *